(12) United States Patent
Shuman et al.

(10) Patent No.: US 11,291,497 B2
(45) Date of Patent: Apr. 5, 2022

(54) ABLATION NEEDLE WITH A SEMIPERMEABLE RING

(71) Applicant: SPIRATION, INC., Redmond, WA (US)

(72) Inventors: Brandon Shuman, Kirkland, WA (US); Zoie Engman, Redmond, WA (US)

(73) Assignee: Gyrus ACMI, Inc., Westborough, MA (US)

(*) Notice: Subject to any disclaimer, the term of this patent is extended or adjusted under 35 U.S.C. 154(b) by 234 days.

(21) Appl. No.: 16/493,580

(22) PCT Filed: Mar. 16, 2017

(86) PCT No.: PCT/US2017/022688
§ 371 (c)(1),
(2) Date: Sep. 12, 2019

(87) PCT Pub. No.: WO2018/169539
PCT Pub. Date: Sep. 20, 2018

(65) Prior Publication Data
US 2020/0030023 A1    Jan. 30, 2020

(51) Int. Cl.
*A61B 18/14* (2006.01)
*A61B 18/00* (2006.01)
*A61B 18/12* (2006.01)

(52) U.S. Cl.
CPC ............ *A61B 18/1477* (2013.01); *A61B 2018/00541* (2013.01); *A61B 2018/00577* (2013.01); *A61B 2018/126* (2013.01); *A61B 2018/1472* (2013.01)

(58) Field of Classification Search
CPC ...... A61B 18/1477; A61B 2018/00541; A61B 2018/00577; A61B 2018/126; A61B 2018/1472; A61B 2018/162
See application file for complete search history.

(56) References Cited

U.S. PATENT DOCUMENTS

| | | | |
|---|---|---|---|
| 6,358,247 B1 * | 3/2002 | Altman | A61B 18/1492 606/41 |
| 6,770,070 B1 * | 8/2004 | Balbierz | A61B 10/04 600/566 |
| 7,393,351 B2 | 7/2008 | Woloszko et al. | |
| 8,414,655 B2 | 4/2013 | Alferness et al. | |
| 9,078,608 B2 | 7/2015 | Kamath et al. | |

(Continued)

OTHER PUBLICATIONS

International Search Report, PCT/2017/022688, dated Dec. 12, 2017.

*Primary Examiner* — Michael F Peffley
(74) *Attorney, Agent, or Firm* — Clements Bernard Baratta Walker; Michael S. Smith

(57) ABSTRACT

An ablation needle apparatus (10) for delivering ablation energy (20) to a subject (40) comprising a hypotube with a proximal and distal end and having a hollow lumen, including a puncture member and a first electrode disposed at the distal end of the hypotube; a second electrode disposed within the hollow lumen; and a first ring member disposed about the second electrode and slidably holding the second electrode apart from the first electrode; wherein the first ring member comprises a semipermeable structure that allows for the passage of a gas and resists the passage of a liquid from the distal end to the proximal end of the hypotube.

11 Claims, 5 Drawing Sheets

(56) References Cited

U.S. PATENT DOCUMENTS

| | | | |
|---|---|---|---|
| 2005/0234443 A1* | 10/2005 | Rioux | A61B 18/00 606/41 |
| 2008/0319436 A1* | 12/2008 | Daniel | A61B 18/1487 606/33 |
| 2012/0296423 A1* | 11/2012 | Caffey | A61F 2/1662 623/6.12 |
| 2015/0272662 A1 | 10/2015 | Shuman | |

* cited by examiner

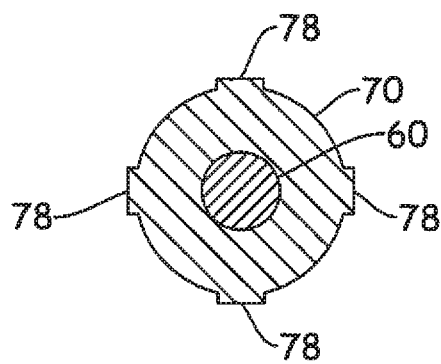
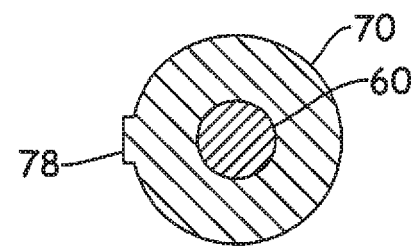
Fig. 14  Fig. 15
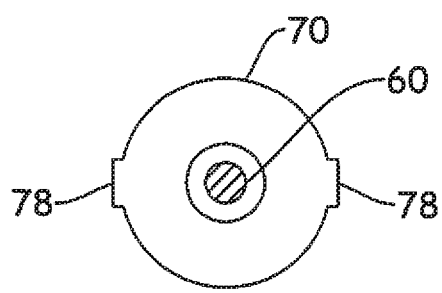
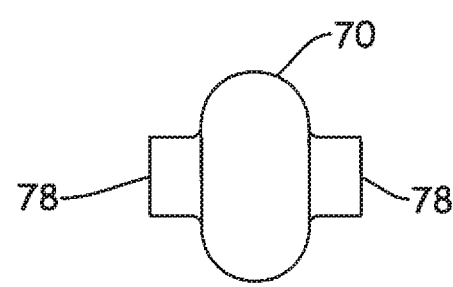
Fig. 16  Fig. 17
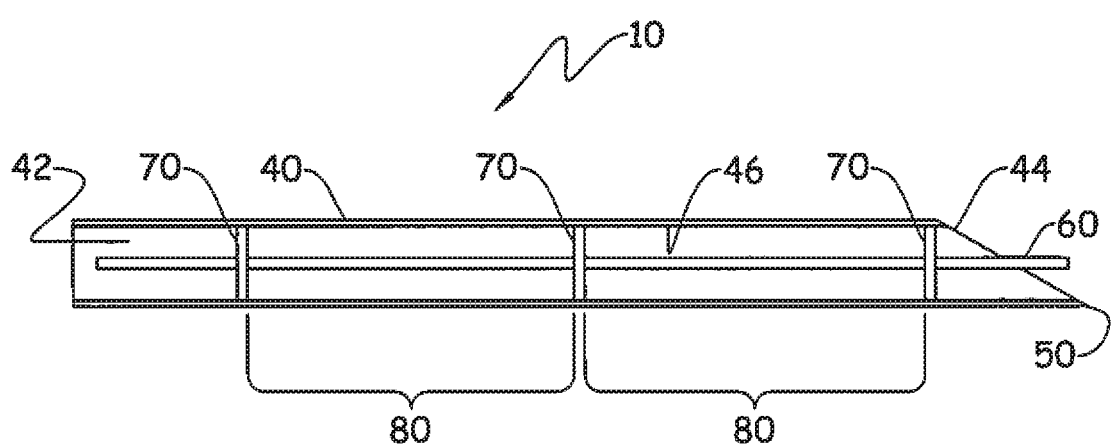
Fig. 18

ABLATION NEEDLE WITH A SEMIPERMEABLE RING

FIELD

The present teachings generally relate to an improved needle assembly, more particularly an improved ablation needle assembly including a slidable semipermeable ring.

BACKGROUND

The present teachings are predicated upon providing an improved ablation needle assembly/apparatus that allows a user to more easily deploy a two-electrode device (bipolar) and a conductive fluid for electrosurgical treatment of a subject's lung. Currently, there are a number of devices that are on the market that are directed at this function, for example: Habib HBV device and Olympus Celon Prosurge, although these devices are structurally very different than the present invention disclosed herein. Patents and publications related to these known devices and/or methods and/or technology area include: U.S. Pat. Nos. 7,393,351; 8,414,655; and 9,078,608, the teachings of which are expressly incorporated by reference herein in their entirety for all purposes.

It is well known, in this field, that bipolar ablation generally requires delivery of high frequency electrical energy to the desired treatment area. In most cases, for this treatment to be most effective, two opposing electrodes are delivered to the treatment area, a conductive fluid (e.g. saline) is introduced, then high frequency electrical energy is applied. It is believed that proper placement of the electrodes and efficient delivery of the conductive fluid can be challenging.

It would be attractive to have an ablation needle assembly/apparatus that functions to allow for proper placement of the electrodes and efficient delivery of the conductive fluid. I would also be attractive if other fluids (e.g. therapeutic compounds) could also be efficiently delivered with the same assembly/apparatus. What is needed is an improved ablation needle assembly/apparatus that has structural features that can provide for the above stated needs.

SUMMARY

The present teachings/invention meet one or more (if not all) of the present needs by providing an apparatus comprising: An ablation needle apparatus 10 for delivering ablation energy to a subject 30 comprising: a hypotube 40 with a proximal and distal end and having a hollow lumen 42, including a puncture portion 44 and a first electrode 50 disposed at the distal end of the hypotube; a second electrode 60 disposed within the hollow lumen; and a first ring member 70 disposed about the second electrode and slidably holding the second electrode apart from the first electrode; wherein the first ring member comprises a semipermeable structure that allows for the passage of a gas and resists the passage of a liquid from the distal end to the proximal end of the hypotube.

The present teachings/invention also may include one or more of the following: a second ring member disposed proximal the first ring member and a third ring member disposed proximal the second ring member, creating a first and second chamber; the first ring member acts as a tissue stop when the second electrode is slidably deployed into the subject and forces the puncturing member in a proximal direction creating a gap G between a distal end of the puncturing member and a proximal side of the first ring; the hollow lumen and the first ring member include a key feature 48,78 that interlocks them in a fixed axial and radial relationship; the gas comprises air and the liquid comprises at least a saline solution.

The present teachings provide improved ablation needle assembly/apparatus.

BRIEF DESCRIPTION OF THE DRAWINGS

FIG. 14 illustrates a front view of a ring structure embodiment with keying features and the second electrode.
FIG. 15 illustrates a front view of another ring structure embodiment with keying features and the second electrode.
FIG. 16 illustrates a front view of another ring structure embodiment with keying features and the second electrode.
FIG. 17 illustrates a side view of the embodiment of FIG. 16
FIG. 18 illustrates a side view of an apparatus with two chambers.

DETAILED DESCRIPTION

Figure 1:
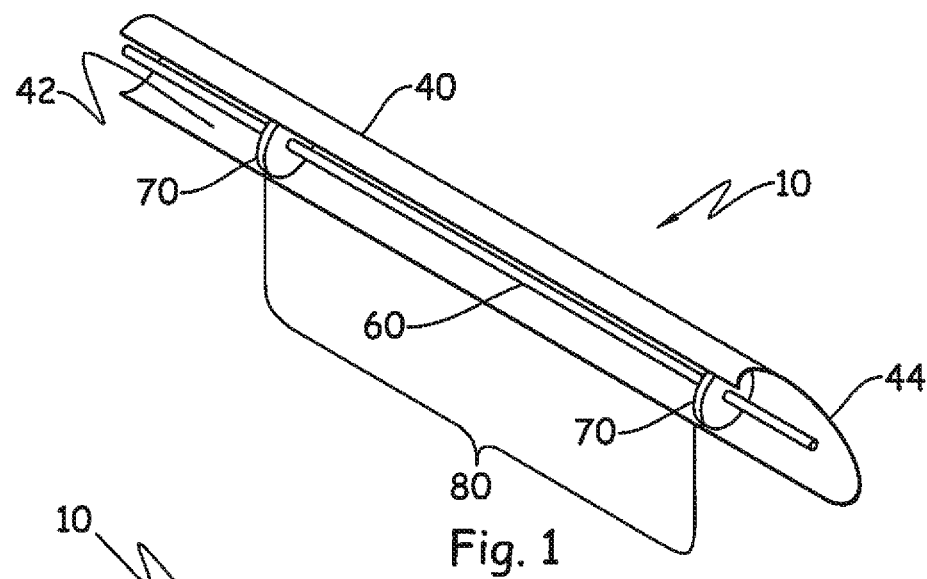
FIG. 1 illustrates a perspective view of one embodiment of the present invention.

The explanations and illustrations presented herein are intended to acquaint others skilled in the art with the invention, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings are directed to an improved ablation needle assembly/apparatus. The improved ablation needle assembly/apparatus functions to allow for proper placement of the electrodes and efficient delivery of the conductive fluid to the desired treatment portion of the lung. It is contemplated that it can allow for the passage of air out of the needle while efficiently delivering the conductive (or other) fluid to the treatment area. It is also contemplated that portions of the device can aid in placement of at least one of the electrodes via a tissue stop feature/function. Furthermore, the apparatus is configured to maintain separation between the first and second electrode before, during and after use. The present invention employs a unique central ring configuration to accomplish some, if not all, the desired performance improvements. Disclosed herein is additional details of the improved apparatus including illustrative examples and preferred embodiments.

Ablation Needle Assembly/Apparatus 10

It is contemplated that the present invention is an improved ablation needle assembly/apparatus 10. This improved apparatus 10 is principally designed to be used in treatment of lung tissue, but may be adapted for ablation procedures in other bodily tissue. It is generally used in the body 20 of a subject 30 to provide bipolar electrical ablation treatment to targeted areas and/or tissue. The assembly/apparatus 10 may be comprised of a number of components that form an assembly. Included may be at least a hypotube 40, a plurality of electrodes (e.g. at least a first 50 and second electrode 60), and one or more ring structures/members 70. Preferably, the hypotube 40 includes a hollow lumen 42, a puncture portion 44 disposed at a distal end, and having the first electrode disposed at or near the distal end (or as part of the puncture portion 44). Additionally, it is contemplated that the second electrode is disposed at least partially within the lumen 42, when not deployed, and disposed at least partially outside of the lumen 42 when deployed.

It is contemplated that one or more ring structures 70 are slidably disposed inside the lumen 42 and hold the second electrode 60 away from the inside wall 46 of the lumen 42. It is also contemplated that the one or more ring structures 70 may act as an axial stop for the second electrode when deployed, also known as a tissue stop. Functionally, when deployed, the distal most of the one or more ring structures 70 would abut the tissue being treated and may prevent the second electrode 60 from penetrating any further into the tissue. Additionally, when deployed, a gap G can be created between the ring structure and part of the puncture portion 44, thus allowing free flow of fluid at the end of the lumen 42. In a preferred embodiment the gap G has a axial dimension D that ranges from about 0.1 mm to 0.5 mm, more preferably from about 0.1 mm to 5 mm, and most preferably from about 0.1 mm to 10 mm.

Airway 32/Subject 30

It is contemplated that the improved ablation needle assembly/apparatus 10 is intended to be used to provide ablation energy to a subject 40 (e.g. human patient, body 20) to treat selective tissue. In a preferred embodiment, the apparatus 10 can be used to treat tissue in an airway 32 of the subject 40, for example to ablate cancerous lung tissue.

Hypotube 40

It is contemplated that the apparatus 10 may include a hypotube 40 that functions as a base structure of the apparatus 10. The hypotube 40 may provide for a connection point for one or more of the other components, such as the puncture portion 44 and the ring structure(s) 70. The hypotube 40 may be constructed of any number of bio-compatible materials, such as stainless steel, nitinol, polymeric materials, or any combination thereof. It is contemplated that the hypotube 40 includes a hollow lumen 42 that generally is disposed about the central axis. The hypotube may have outer walls 46 that are solid, or have cuts that function to allow or aid in bending of the apparatus 10.

Figure 11:
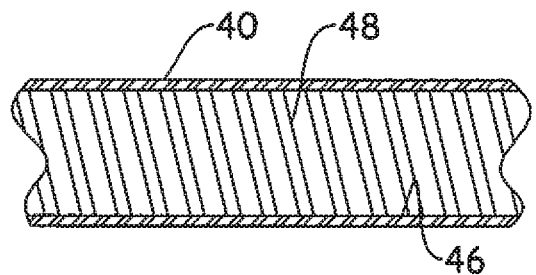
FIG. 11 illustrates a side view of another embodiment including keying features.
Figure 12:
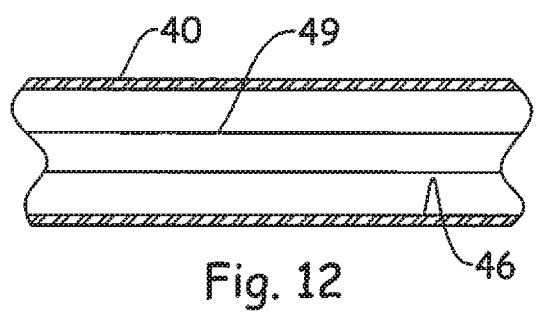
FIG. 12 illustrates a side view of an embodiment including tube channel features.
Figure 13:
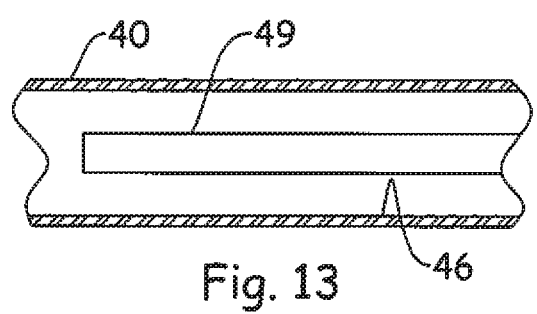
FIG. 13 illustrates a side view of another embodiment including tube channel features.

It is contemplated that they may also be tube keying features 48 in the walls 46 that mate/correspond with ring keying features 78 of the ring structure 70. Functionally, the keying features 48/78 may provide a set direction or limited travel during deployment of the ring 70 and the second electrode 60. For example, the keying features 48/78 may cause the electrode 60/ring 70 to have a spiral motion as it moves towards the distal end of the hypotube 40 (see FIG. 11 generally). It is also contemplated that there may be a tube channel 49 in the hypotube 40 that allows for a gap between the ring 70 and the wall 46. In addition, or as an alternative, the ring structure 70 may have one or more gaps ("ring gap 79"), at least locally, that allows for a gap between the ring 70 and the wall 46.

It is also contemplated that the hypotube 40 may include a window 85 with a slidable cover 86. This may be useful for the case where treatment material 81 are to be introduced via the window 85 (see 84 for flow of material 81).

First Electrode 50

It is contemplated that the apparatus 10 may include a first electrode 50. The first electrode 50 functions as the first of two electrodes in a bipolar electrode system for supplying ablation energy to targeted tissues. The first electrode 50 may be disposed at or near the distal end of the apparatus 10. The first electrode 50 may be disposed on, near, or integral with the puncture portion 44. The electrode 50 may be constructed of any number of electrically conductive and bio-compatible materials, such as stainless steel, nitinol, conductive polymeric materials, or any combination thereof. In a preferred embodiment, the electrode 50 is constructed of stainless steel.

It is contemplated that the first electrode 50 may have one or more geometric configurations. Functionally, it should have enough surface area given the electrode material selection to provide sufficient ablation energy for the desired treatment. Given the preferred material (stainless steel), it is preferred that the surface area range between at least about 3 mm$^2$ to 4 mm$^2$, more preferably between about 2 mm$^2$ and 5 mm$^2$, and most preferably between about 1 mm$^2$ and 6 mm$^2$.

Second Electrode 60

It is contemplated that the apparatus 10 may include a second electrode 60. The second electrode 60 functions as the second of two electrodes in a bipolar electrode system for supplying ablation energy to targeted tissues. The second electrode 60, may be disposed at or near the distal end of the apparatus 10, particularly when deployed for treatment. The second electrode may be disposed within the lumen 42 and held away from the wall 46 of the hypotube 40 by the ring structure 70. The electrode 60 may be constructed of any number of electrically conductive and bio-compatible materials, such as stainless steel, nitinol, conductive polymeric materials, or any combination thereof. In a preferred embodiment, the electrode 60 is constructed of stainless steel.

It is contemplated that the second electrode 60 may have one or more geometric configurations, but preferably is generally shaped in a shaft-like configuration. Functionally, it should have enough surface area given the electrode material selection to provide sufficient ablation energy for the desired treatment. Given the preferred material (stainless steel), it is preferred that the surface area range between at least about 2 mm^2 and 5 mm^2, and most preferably between about 1 mm^2 and 6 mm^2.

Ring Structure(s) 70

It is contemplated It is contemplated that the apparatus 10 may include one or more ring structures 70. The ring(s) 70 have several functions. Firstly, to substantially hold the second electrode 60 away from the wall 46 of the hypotube 40. Secondly, to control the flow of fluids (gaseous and liquids) within the hollow lumen 42. Thirdly, to act as a tissue stop that helps control the penetration of the electrode 60 into the tissue being targeted for treatment.

The ring structures 70 may be slidably disposed within the hollow lumen 42, and can move at least axially along the lumen 42. The rings 70 may include ring keying features 78 that can control axial and rotational movement (e.g. interlocking them in a fixed axial and radial relationship). The rings 70 may also include a configuration that provides for a ring gap 79, a gap between the wall 46. The rings 70 may also be comprised at least partially of a semipermeable structure or membrane that allows for the flow of select fluids and prevents the flow of select fluids through the rings 70. For example, the semipermeable structure may allow for gaseous material (e.g. air) to flow through the structure while preventing liquid material (e.g. saline solution) to flow. A known example of one type of semipermeable structure includes GORE-TEX® products, from W. L. Gore & Associates, Inc.

It is contemplated that there may be more than one ring structure 70 included in the apparatus 10. In configurations that include multiple rings, a chamber 80 may be formed between two adjacent rings 70 (distal ring 70 nearer the distal end of the apparatus 10, nearer the puncture portion 44). It is contemplated that these chambers 80 may be utilized to hold treatment materials (81, 82), particularly liquid materials (hold until the electrode 60 is deployed). Examples of such treatment materials may include: Saline Solution, Chemotherapy medicines, Antibiotics, or other liquid based medical treatment materials. It is contemplated that the chamber 80 may be pre-loaded with the treatment materials (81, 82) prior to use in the subject 30.

Illustrative Examples

Figure 2:
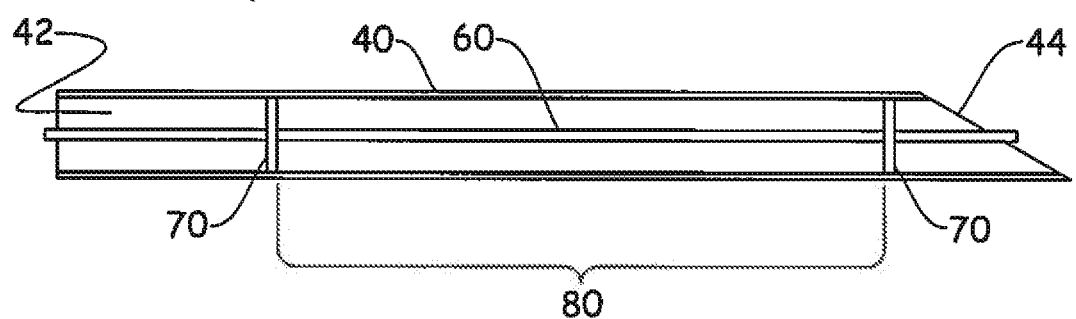
FIG. 2 illustrates a side view of FIG. 1
Figure 3:
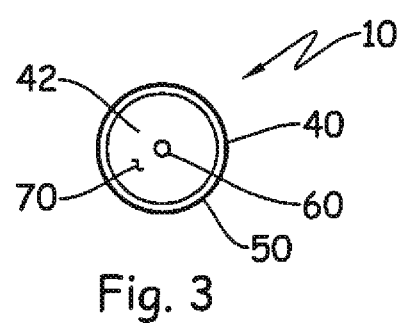
FIG. 3 illustrates a front view of FIG. 1
Figure 4:
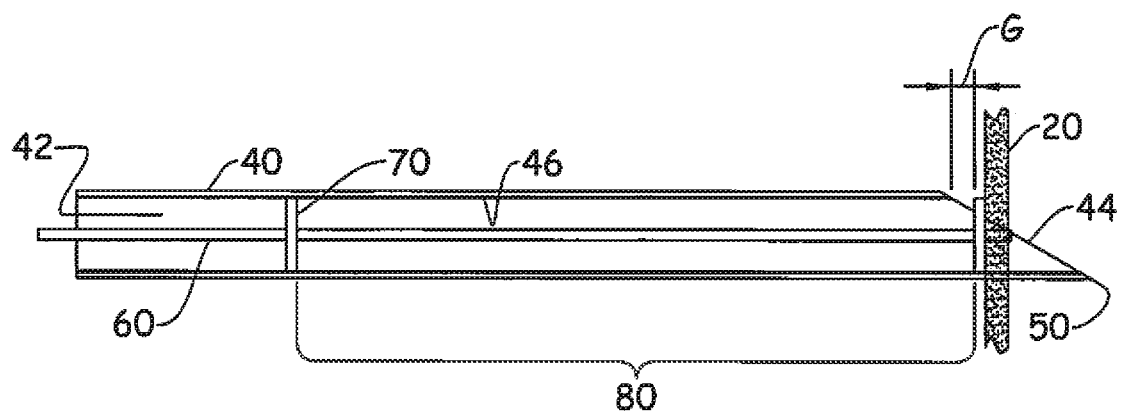
FIG. 4 illustrates a side view of one embodiment/one level of deployment of the present invention.
Figure 5:
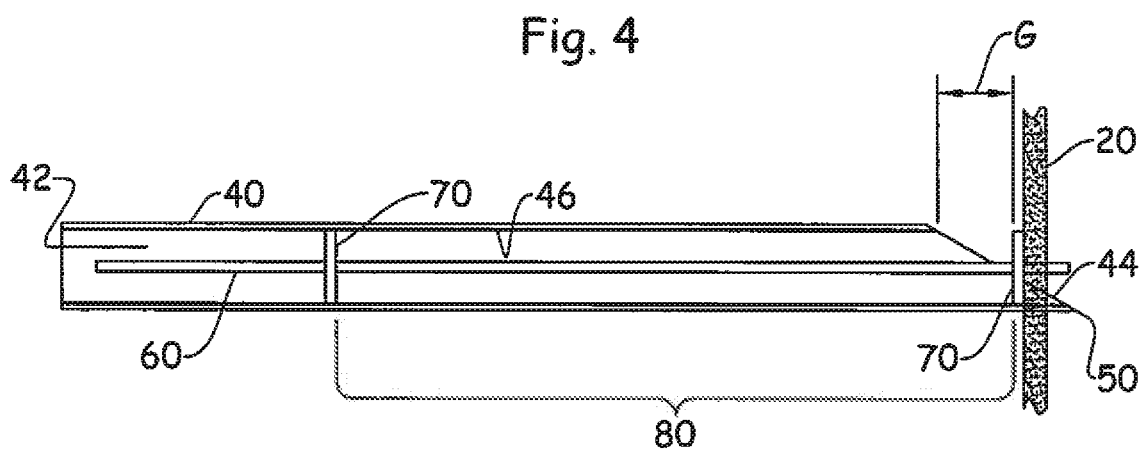
FIG. 5 illustrates a side view of one embodiment/another level of deployment of the present invention.
Figure 6:
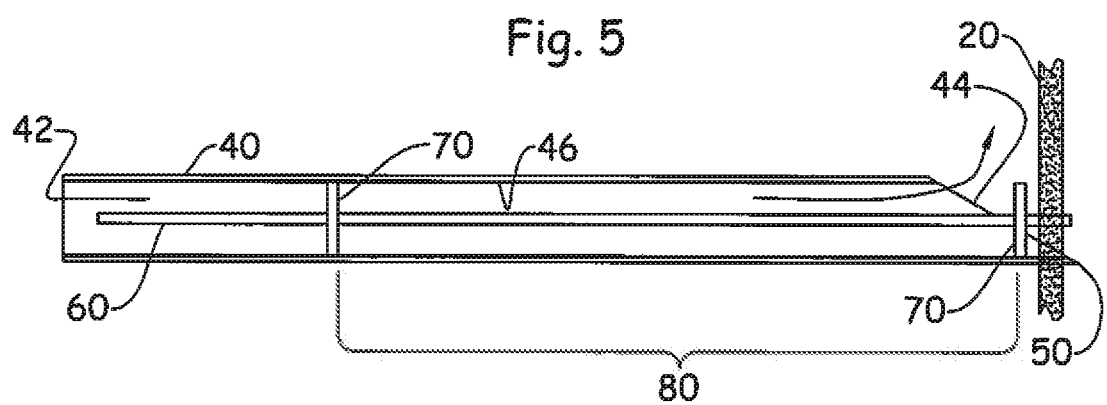
FIG. 6 illustrates a side view of one embodiment/another level of deployment of the present invention.
Figure 7:
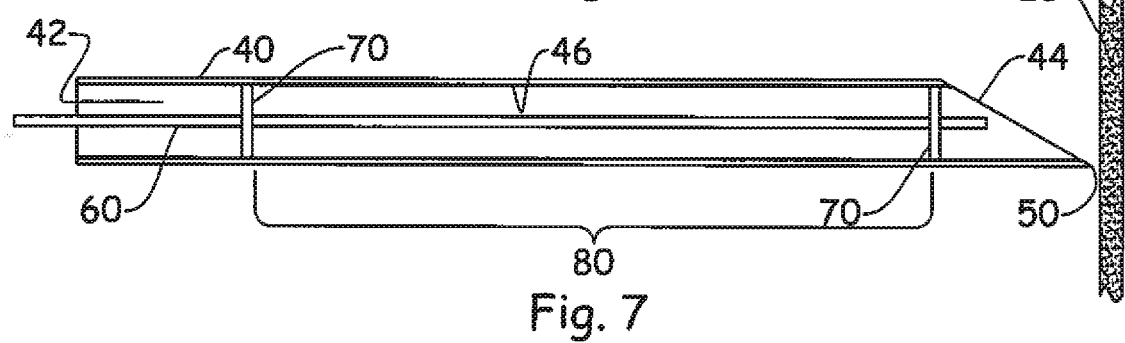
FIG. 7 illustrates a side view of one embodiment/another level of deployment of the present invention.

FIGS. 1, 2 and 3 illustrates three views of an exemplary apparatus 10. Shown is a portion of the hypotube 40 with a hollow lumen 42 and the puncture portion 42. Also shown is the first and second electrodes 50, 60, two ring structures 70 and a chamber 80 formed therebetween.

FIGS. 4 through 7 show the exemplary apparatus 10 of FIGS. 1-3 in various positions as being deployed in a body 20. Shown in these views is the gap G, the hypotube wall 46, and the distal ring structure 70 acting as a tissue stop (FIGS. 4 and 5) as it comes in contact with the body 20.

Figure 8:
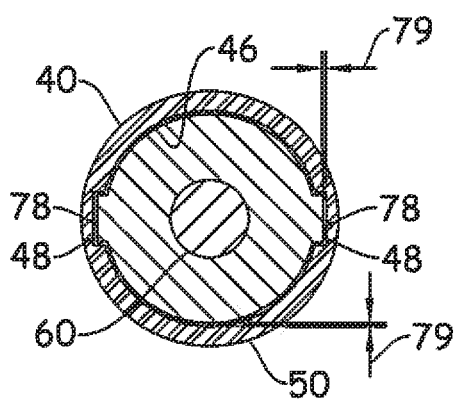
FIG. 8 illustrates a front view of an embodiment including a ring gap and keying features.
Figure 9:
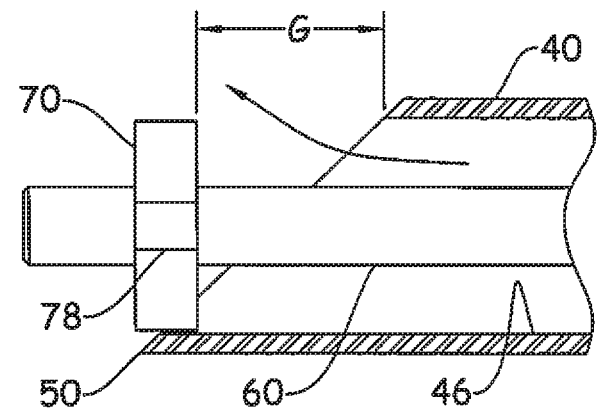
FIG. 9 illustrates a side view of an embodiment including keying features.
Figure 10:
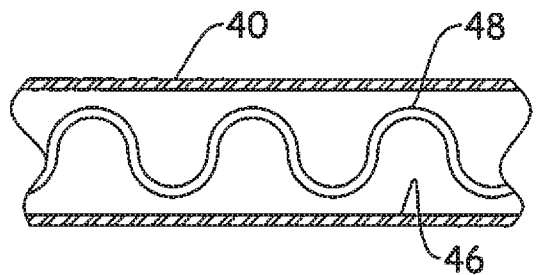
FIG. 10 illustrates a side view of another embodiment including keying features.

FIGS. 8 through 17 shown various embodiments of potential keying tube features 48, ring keying features 78, and tube channels 49. Also, shown in FIG. 8, is an embodiment of the ring gap 79, a space between the hypotube wall 46 and the ring structure 70.

FIG. 18 shows an embodiment of the apparatus that includes three ring structures 70 and two chambers 80.

Figure 19:
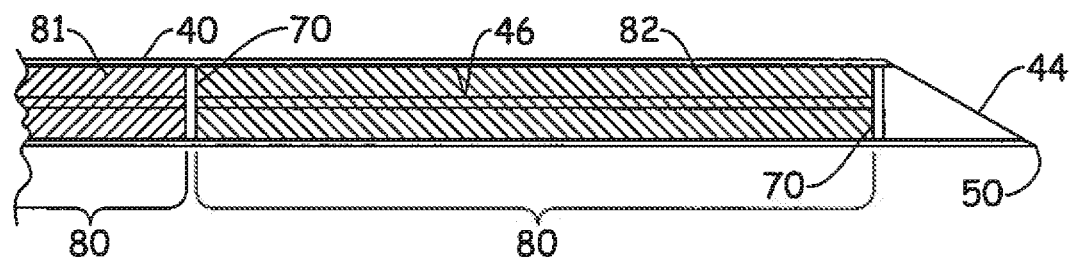
FIG. 19 illustrates a side view of another apparatus with two chambers.
Figure 20:
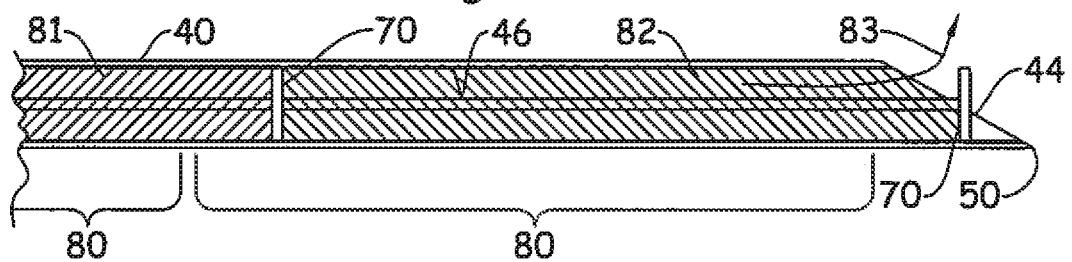
FIG. 20 illustrates a side view of the apparatus of FIG. 19 with the distal ring deployed.

FIGS. 19 and 20 show an embodiment where two chambers 80 that hold two treatment materials 81, 82. FIG. 19 shows the distal treatment material flowing out (see arrow 83) and FIG. 20 shows the proximal treatment material 81 flowing out 84. This second flow happens when the proximal ring 70 is pushed essentially to the distal ring 70.

Figure 21:
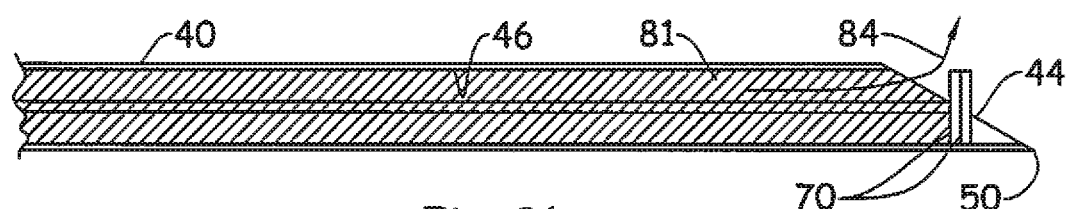
FIG. 21 illustrates a side view of the apparatus of FIG. 19 with the distal ring and the proximal ring deployed.
Figure 22:
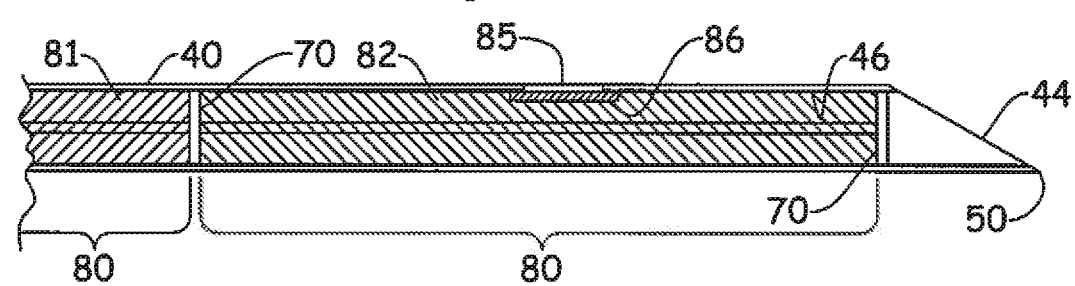
FIG. 22 illustrates a side view of another apparatus with two chambers and a window and a cover member.
Figure 23:
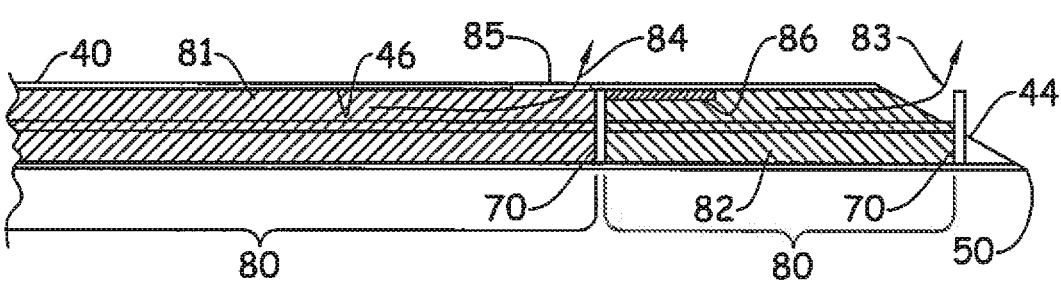
FIG. 23 illustrates a side view of the FIG. 22 apparatus with two chambers and a window, a cover member deployed, and with the distal ring deployed.

FIGS. 21 and 22 show an embodiment that includes two chambers 80, a window 85 in the wall 46 of the hypotube 40 with a slidable cover 86. In this embodiment, the slidable window is moved distally by the proximal ring 70 to allow for the flow 84 of the proximal treatment material 81 out of the open window 85 (see FIG. 22). It is contemplated that at least in this embodiment or any of the earlier described ones, the first and/or second electrodes 50, 60 may be simple first and/or second needle members that have no function as electrodes. In that instance, the apparatus 10 functions more as a unique treatment delivery device without the ablation function.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

improved ablation needle assembly/apparatus/needle apparatus 10
  body 20
  subject 30
  hypotube 40
  hollow lumen 42
  puncture portion 44
  wall (hypotube) 46
  tube keying feature 48
  tube channel 49
  first electrode 50
  second electrode/needle member 60
  ring structures 70
  ring keying features 78
  ring gap 79
  Chamber 80
  Proximal treatment material 81
  Distal treatment material 82
  Distal material flow 83
  Proximal material flow 84
  Window 85
  Slidable cover 86
  Gap G

We claim:

1. An ablation needle apparatus for delivering ablation energy to a subject comprising:
a hypotube with a proximal and distal end and having a hollow lumen, including a puncture portion and a first electrode disposed at the distal end of the hypotube;
a second electrode disposed within the hollow lumen; and
a first ring member disposed about the second electrode and slidably holding the second electrode apart from the first electrode;
wherein the first ring member comprises a semipermeable structure that allows for the passage of a gas and resists the passage of a liquid from the distal end to the proximal end of the hypotube.

2. The ablation needle apparatus of claim 1 further comprising:
a second ring member disposed proximal the first ring member and a third ring member disposed proximal the second ring member, creating a first and second chamber.

3. The ablation needle apparatus of claim 1 further wherein:
the first ring member acts as a tissue stop when the second electrode is slidably deployed into the subject and forces the puncturing portion in a proximal direction creating a gap between a distal end of the puncturing portion and a proximal side of the first ring.

4. The ablation needle apparatus of claim 1 further comprising:
the hollow lumen and the first ring member include a key feature that interlocks them in a fixed axial and radial relationship.

5. The ablation needle apparatus of claim 1 further wherein:
the gas comprises air and the liquid comprises at least a saline solution.

6. The ablation needle apparatus of claim 1 further comprising:
the hollow lumen and the first ring member include a key feature that interlocks them in a fixed axial and radial relationship.

7. The ablation needle apparatus of claim 1 further wherein:
the gas comprises air and the liquid comprises at least a saline solution.

8. A needle apparatus for use in a subject comprising:
a hypotube with a proximal and distal end and having a hollow lumen defined by a wall, including a puncture portion disposed at the distal end of the hypotube;
a needle member disposed within the hollow lumen; and
a first ring member disposed about the needle member and slidably holding the needle member apart from the wall;
wherein the first ring member comprises a semipermeable structure that allows for the passage of a gas and resists the passage of a liquid from the distal end to the proximal end of the hypotube.

9. The needle apparatus of claim 8 further comprising:
a second ring member disposed proximal the first ring member and a third ring member disposed proximal the second ring member, creating a first and second chamber.

10. The needle apparatus of claim 9 further comprising:
a window covered by a slidable cover disposed within the second chamber.

11. The ablation needle apparatus of claim 8 further wherein:
the first ring member acts as a tissue stop when the hypotube is deployed into the subject and forces the puncture portion in a proximal direction creating a gap between a distal end of the puncture portion and a proximal side of the first ring.

* * * * *